(12) United States Patent
Baliktay et al.

(10) Patent No.: US 7,802,611 B2
(45) Date of Patent: *Sep. 28, 2010

(54) PROCESS FOR PRODUCING AN IMPLANT FROM A TITANIUM ALLOY, AND CORRESPONDING IMPLANT

(75) Inventors: Sevki Baliktay, Berlin (DE); Arnold Keller, Kayhude (DE)

(73) Assignee: Waldemar Link GmbH & Co., KG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/370,231

(22) Filed: Mar. 8, 2006

(65) Prior Publication Data

US 2007/0068647 A1    Mar. 29, 2007

Related U.S. Application Data

(60) Provisional application No. 60/659,093, filed on Mar. 8, 2005.

(51) Int. Cl.
*B22C 9/04* (2006.01)
*C22C 14/00* (2006.01)

(52) U.S. Cl. .................. 164/76.1; 164/516; 420/421

(58) Field of Classification Search ............. 164/76.1; 420/417, 421
See application file for complete search history.

(56) References Cited

U.S. PATENT DOCUMENTS

| | | | | |
|---|---|---|---|---|
| 4,197,643 A | * | 4/1980 | Burstone et al. | 433/20 |
| 4,612,066 A | * | 9/1986 | Levin et al. | 148/669 |
| 5,226,982 A | | 7/1993 | Eylon et al. | |
| 5,947,723 A | * | 9/1999 | Mottate et al. | 433/8 |
| 6,238,491 B1 | | 5/2001 | Davidson et al. | |
| 6,409,852 B1 | * | 6/2002 | Lin et al. | 148/669 |
| 7,288,111 B1 | | 10/2007 | Holloway et al. | |
| 2002/0179197 A1 | | 12/2002 | Lin et al. | |
| 2004/0088056 A1 | | 5/2004 | Lewallen | |
| 2004/0136859 A1 | | 7/2004 | Chern Lin et al. | |
| 2004/0168751 A1 | | 9/2004 | Wu | |
| 2006/0157543 A1 | | 7/2006 | Abkowitz et al. | |
| 2006/0225818 A1 | | 10/2006 | Baliktay | |

2006/0235536 A1    10/2006   Baliktay et al.

OTHER PUBLICATIONS

Phase Diagram of Mo-Ti, Metal Handbook, vol. 8, p. 321, ASM, 8th edition, 1973).*
"Comparison Among Mechanical Properties of Investment-cast c.p. Ti, Ti-6Al-7Nb and Ti-15Mo-1Bi alloys" by Lin et al., Material Transactions, vol. 45, No. 10 (2004), Oct. 2004, The Japan Institute of Metals.*
Donachie et al. (2002) "Titanium-a Technical Guide," ASM International, pp. 39-42.
"Annealing (Mettalurgy)", Wikipedia, Aug. 2009.
Baliktay, S. et al.; U.S. Office Action, mailed Oct. 17, 2007, directed to U.S. Appl. No. 11/370,163; (8 pages).
Baliktay, S. et al.; U.S. Office Action, mailed Dec. 16, 2008, directed to U.S. Appl. No. 11/370,163; (9 pages).
Baliktay, S. et al.; U.S. Office Action, mailed Jun. 1, 2009, directed to U.S. Appl. No. 11/370,163; (8 pages).
Baliktay, S., U.S. Office Action, mailed Aug. 21, 2007, directed to U.S. Appl. No. 11/370,232; (6 pages).
Baliktay, S., U.S. Office Action, mailed Mar. 6, 2008, directed to U.S. Appl. No. 11/370,232; (8 pages).
Baliktay, S., U.S. Office Action, mailed Oct. 7, 2008, directed to U.S. Appl. No. 11/370,232; (8 pages).
Baliktay, S., U.S. Office Action, mailed Mar. 30, 2009, directed to U.S. Appl. No. 11/370,232; (8 pages).
Baliktay, S., U.S. Office Action, mailed Sep. 8, 2009, directed to U.S. Appl. No. 11/370,232; (11 pages).
Baliktay, S. et al., U.S. Office Action mailed Nov. 25, 2009, directed to U.S. Appl. No. 11/370,163; 8 pages.
Baliktay; U.S. Office Action, mailed Dec. 15, 2009, directed to U.S. Appl. No. 11/370,232; (9 pages).

* cited by examiner

*Primary Examiner*—Kuang Lin
(74) *Attorney, Agent, or Firm*—Morrison & Foerster LLP

(57) ABSTRACT

A process for producing a medical implant from a titanium alloy, by investment-casting a β-titanium alloy in a casting mold which corresponds to the implant that is to be produced, hot isostatic pressing, solution annealing, and then quenching. The corresponding medical implant is produced from the titanium alloy using the investment casting process, thus allowing economical production of objects from β-titanium alloys. The β-titanium alloy and has a mean grain size of at least 0.3 mm. It is possible to combine the advantageous properties of β-titanium alloys, in particular their excellent mechanical properties, with the advantages of producing objects by the precision casting process, thus enabling even implants of complex shapes, such as femur parts of hip joint prostheses, which have heretofore been impossible (economically) to produce by conventional forging processes, to be produced from a β-titanium alloy.

7 Claims, 4 Drawing Sheets

| Solution annealing temperature [°C] | Tensile strength Rm [N/mm²] | 0.2% Proof stress Rp [N/mm²] | Elongation at break A5 [%] | Reduction of area after fracture Z [%] | Modulus of elasticity E [kN/mm²] | Hardness HB30 |
|---|---|---|---|---|---|---|
| 700 | 920 | 916 | 2.1 | 10 | 68 | 285 |
| 740 | 841 | 665 | 7.5 | 19.3 | 66 | 278 |
| 760 | 790 | 545 | 18.5 | 23.4 | 65.4 | 268 |
| 780 | 735.3 | 520 | 27.4 | 40 | 63.7 | 260 |
| 800 | 725 | 505 | 37.6 | 52 | 59.4 | 255 |

Fig. 6

PROCESS FOR PRODUCING AN IMPLANT FROM A TITANIUM ALLOY, AND CORRESPONDING IMPLANT

REFERENCE TO RELATED APPLICATION

This application claims priority from U.S. Provisional Application Ser. No. 60/659,093, filed Mar. 8, 2005, the entire content of which is incorporated herein by reference.

FIELD OF THE INVENTION

The invention relates to a process for producing a medical implant from a titanium alloy, and to a corresponding implant.

BACKGROUND OF THE INVENTION

Titanium alloys are in increasingly widespread use as material for the production of implants. The benefits of this material for use as prostheses include important properties such as a high mechanical load-bearing capacity, a high chemical stability and, not least, excellent biocompatibility. With regard to the material properties aspect, titanium alloys are the material of choice for many different types of implants, including bone plates, pins, artificial knee and hip joints as well intervertebral disk prostheses.

The prior art has disclosed various processes for producing the implants. The choice of a suitable process depends not only on the type of implant to be produced but also on the titanium alloy used in each instance. For shaping purposes, there are two main processes used for titanium alloys, namely forging, on the one hand, and investment casting, on the other hand. In principle, titanium alloys are forging alloys (Peters/Leyens: Titan and Titanlegierungen [Titanium and titanium alloys], Wiley-VCH-Verlag, 2002). However, investment casting has the advantage of allowing even complex shapes to be produced easily near net shape, whereas these complex shapes cannot be achieved by forging or can only be achieved by joining a plurality of components. However, the investment casting of titanium alloys generally causes problems on account of the high melting point and the high reactivity of titanium; an additional problem is the low density of the alloys. Only a few groups of titanium alloys are suitable for investment casting. These include in particular what are known as α-titanium alloys and some α/β-titanium alloys. From the latter group, in particular alloys comprising vanadium and aluminum, such as TiAl6V4, have become important for the production of implants. Implants, such as joint prostheses or dental implants, can be produced successfully from this alloy by investment casting.

However, there are certain concerns as to the long-term compatibility of the alloying elements which are typically used for α/β-titanium alloys, such as TiAl6V4. Moreover, the modulus of elasticity of these alloys is well above that of natural bone material, which can lead to pathological changes to the bone.

SUMMARY OF THE INVENTION

The invention is based on the object of providing medical implants with which these drawbacks are alleviated.

The solution according to the invention lies in the features of the invention as broadly described herein. Advantageous refinements form the subject matter of the preferred embodiments.

The invention provides a process for producing a medical implant from a titanium alloy, comprising the steps of investment-casting the titanium alloy in a casting mold which corresponds with the implant that to be produced, and according to the invention it is provided that a β-titanium alloy is used, hot isostatically pressed, solution annealed, and then quenched.

The process according to the invention makes it possible to produce medical implants from a β-titanium alloy by investment casting. The possibility of using β-titanium alloys brings with it considerable advantages with regard to medical implants. For example, β-titanium alloys have favorable mechanical properties, in particular a much lower modulus of elasticity than the known α/β-titanium alloys. Whereas the latter usually have moduli of approx. 100 000 N/mm$^2$, with titanium-molybdenum alloys it is possible to achieve moduli which have been virtually halved, at approx. 60 000 N/mm$^2$. Furthermore, the biocompatibility can be increased by using β-titanium alloys. Whereas with the α/β-titanium alloy TiAl6V4 which is frequently used there are certain concerns with regard to toxicity of aluminum or vanadium ions that are released, alloying elements which are harmless from a toxicity perspective, such as molybdenum, can successfully be used for β-titanium alloys. It has been found that in particular with titanium-molybdenum alloys, it is possible to achieve excellent results with regard to the mechanical properties and also with regard to biocompatibility. It is preferable for the molybdenum content or the molybdenum equivalent value to be between 7.5 and 25%, more preferably between 12 and 16%. This allows a meta-stable β-phase to be achieved by rapid cooling after casting. TiMo15 with a molybdenum content of 15% has proven particularly suitable.

Furthermore, the use of β-titanium alloy has the advantage that even implants of complex shape can be produced economically. In general terms, investment casting is a shaping process which can be used to produce even complex shapes economically compared to shaping by forging. However, it has been found that in particular when used with the α- or α/β-titanium alloys known from the prior art, investment casting has been insufficiently able to produce sharp edges on the implants. Consequently, the benefits inherent to investment casting, namely the ability to produce any desired complex shapes, have not been fully realized. In particular in the case of implants, however, it is frequently desirable to provide sharp edges in order to improve the anchoring of the implant. Sharp edges on the implants are very important for cement-free implantation, which is in many cases the preferred option for reasons of the long-term mechanical stability of the implant. Surprisingly, it has been found that the process according to the invention achieves improved mold filling. This means that sharp edges can be achieved with a high quality even for implants of a complex shape. Therefore, the invention gives access not only to implants with more favorable properties with regard to mechanics and biocompatibility, but also with regard to improving the shaping achieved by investment casting.

During the solution annealing, the temperature profile is expediently selected in such a way that the titanium alloy is free of Ω-phases. This counteracts the risk of the mechanical properties being adversely affected by the formation of a Ω-phase.

A temperature below the β-transus temperature, specifically at most 100° C., preferably 40° C., below the β-transus temperature, is expedient for the hot isostatic pressing (HIP). Temperatures in the range from 710° C. to 760° C., preferably of approximately 740° C., at an argon pressure of approximately of 1100° C. to 1200 bar have proven suitable for a titanium-molybdenum alloy with molybdenum content of 15%.

Temperatures of at least 700° C. to 900° C., preferably in the range from 780° C. to 880° C., under an argon shielding gas atmosphere have proven suitable for the solution annealing. In particular at temperatures over 780° C., the ductility of the alloy is improved. There is no need for preliminary age-hardening before or after the hot isostatic pressing. The subsequent quenching preferably takes place in cold water.

It may be advantageous for the object also to be hardened at the end. This allows the modulus of elasticity to be increased further. For this purpose, the hardening preferably takes place in a temperature range from approx. 600° C. to approx. 700° C.

The invention also relates to a medical implant produced in accordance with the above process and to a medical implant in accordance with the further independent claim. This provides a medical implant made from a β-titanium alloy which has a mean grain size of at least 0.3 mm. For further explanation, reference is made to the statements given above.

The following additional comments should be added: the implant may be an orthopedic prosthesis, preferably a joint prosthesis. Joint prostheses are subject to high static and dynamic stresses. The transmission of load to the surrounding bone structure is of particular importance. This should be as physiologically favorable as possible. A critical factor in this context is that unfavorable transmission of load from the prosthesis to the surrounding bone can lead to degeneration of the bone tissue. This by no means infrequently leads to the prosthesis coming loose. Tests have shown that prostheses made from a material with a lower modulus of elasticity produce a loading situation which is more physiological than prostheses made from rigid material. The same applies in particular to prostheses with long shafts, such as the femur part of a hip prosthesis or other joint prostheses. The modulus of elasticity of a conventional titanium alloy, for example TiAl6V4, is approx. 100 000 N/mm², therefore well above the modulus of elasticity of the cortical bone material of approximately 25 000 N/mm². Lower moduli can be achieved with the implant according to the invention. For example, an implant produced according to the invention from TiMo15 has a modulus of elasticity of approx. 60 000 N/mm², i.e. only slightly more than half the modulus of TiAl6V4. This is a major advantage in particular for joint prostheses with long shafts, such as hip, knee, shoulder or elbow prostheses, since the result is a significant improvement with regard to the transmission of force to the bone.

Corresponding considerations also apply to an embodiment of the implant according to the invention as a dental prosthesis.

BRIEF DESCRIPTION OF THE DRAWINGS

The invention is explained below with reference to the drawing, which illustrates an advantageous exemplary embodiment and in which:

FIG. 6 shows a table giving mechanical properties of the titanium alloy which has been processed in accordance with the invention.

DETAILED DESCRIPTION OF THE INVENTION

First of all, a description will be given of a way of carrying out the process according to the invention. The implant produced is explained later on the basis of the example of a femur part of a hip prosthesis.

The starting material is a β-titanium alloy with a molybdenum content of 15% (TiMo15). This alloy is commercially available in the form of billets (ingots).

A first step involves investment casting of the objects which are to be cast. In the present context, an object is to be understood as meaning an implant which has been shaped suitably for its final use, such as endoprostheses, for example hip prostheses or other joint prostheses, or immobile implants, for example plates or pins or dental implants. The term does not encompass billets which are intended for further processing by shaping processes, i.e. in particular does not encompass ingots produced by permanent mold casting for further processing by forging or other shaping processes.

A casting installation is provided for the purpose of melting and casting the TiMo 15. The casting installation is preferably a cold-wall crucible vacuum induction melting and casting installation. An installation of this type can reach the high temperatures which are required for reliable melting of TiMo15 for investment casting. The melting point of TiMo15 is 1770° C. plus a supplement of approx. 60° C. for reliable investment casting. Overall, therefore, a temperature of 1830° C. needs to be reached. The investment casting of the melt is then carried out by means of processes which are known per se, for example using ceramic molds as lost mold. Investment casting techniques of this type are known for the investment casting of TiAl6V4.

Figure 1:
FIG. 1 shows an image of the microstructure in a cast state immediately after casting.

As can be seen from the image (1000 times magnification) in FIG. 1, dendrites are formed and considerable amounts of precipitation occur in inter-dendritic zones. This is a consequence of what is known as the negative segregation of titanium-molybdenum alloys. This effect is based on the specific profile of the liquidus and solidus temperature of titanium-molybdenum alloys. In the melt, the regions with a high molybdenum content solidify first of all, forming the dendrites which can be seen in the figure. This depletes the remainder of the melt, i.e. its molybdenum content drops. The inter-dendritic zones in the cast microstructure have a molybdenum content of below 15%, which can even drop to approx. 10%. As a result of the molybdenum depletion, the inter-dendritic zones lack a sufficient quantity of n-stabilizers, with the result that an increased α/β-transformation temperature is locally established, leading to the precipitations that are readily apparent in FIG. 1.

It is expedient for a surface zone which may form during casting as a hard, brittle layer, known as the (α-case) to be removed by pickling. The thickness of this layer is usually approx. 0.03 mm.

Figure 2:
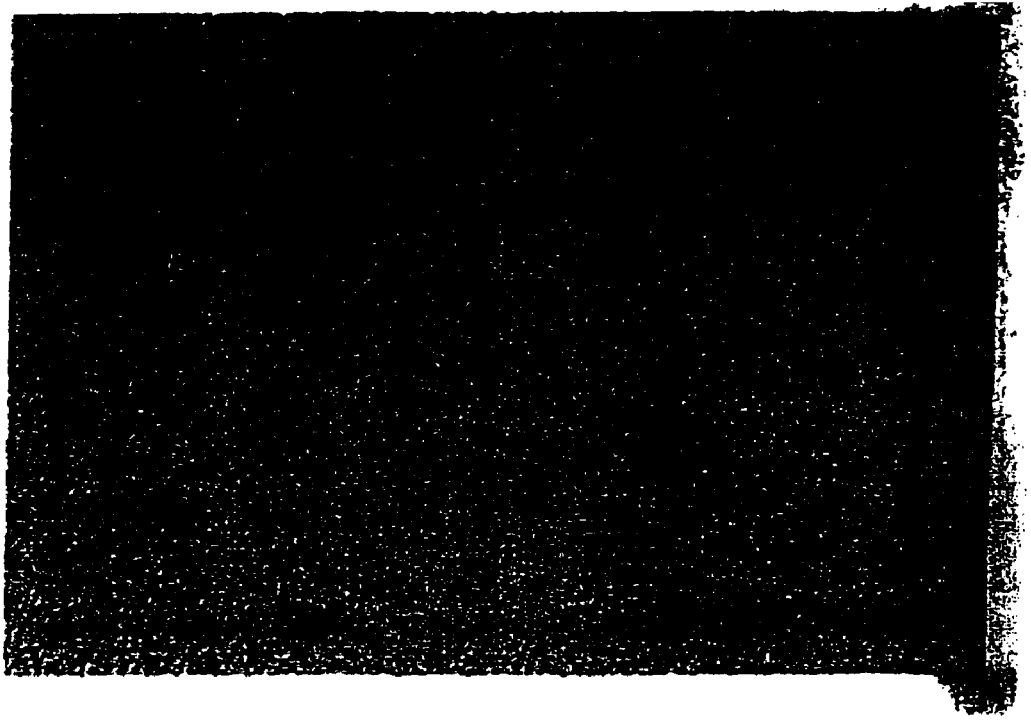
FIG. 2 shows an image of the microstructure after the hot isostatic pressing.

To counteract the unfavorable effect of the negative segregation with the precipitations in the inter-dendritic zones, according to the invention the castings, after the casting molds have been removed following the investment casting, are subjected to a heat treatment. This involves hot isostatic pressing (HIP) specifically at a temperature just below the β-transus temperature. It may be in the range from 710° C. to 760° C. and is preferably approximately 740° C. The pressing is carried out using argon at a pressure of from 1100 to 1200 bar. This causes inter alia the undesirable precipitations in the inter-dendritic zones to be dissolved again. However, fine secondary phases precipitate again during the cooling following hot isostatic pressing, preferentially in the original inter-dendritic zones (cf. FIG. 2, 1000× magnification). This leads to undesirable embrittlement of the materials.

The cast objects have only a low ductility following the hot isostatic pressing.

Figure 3:
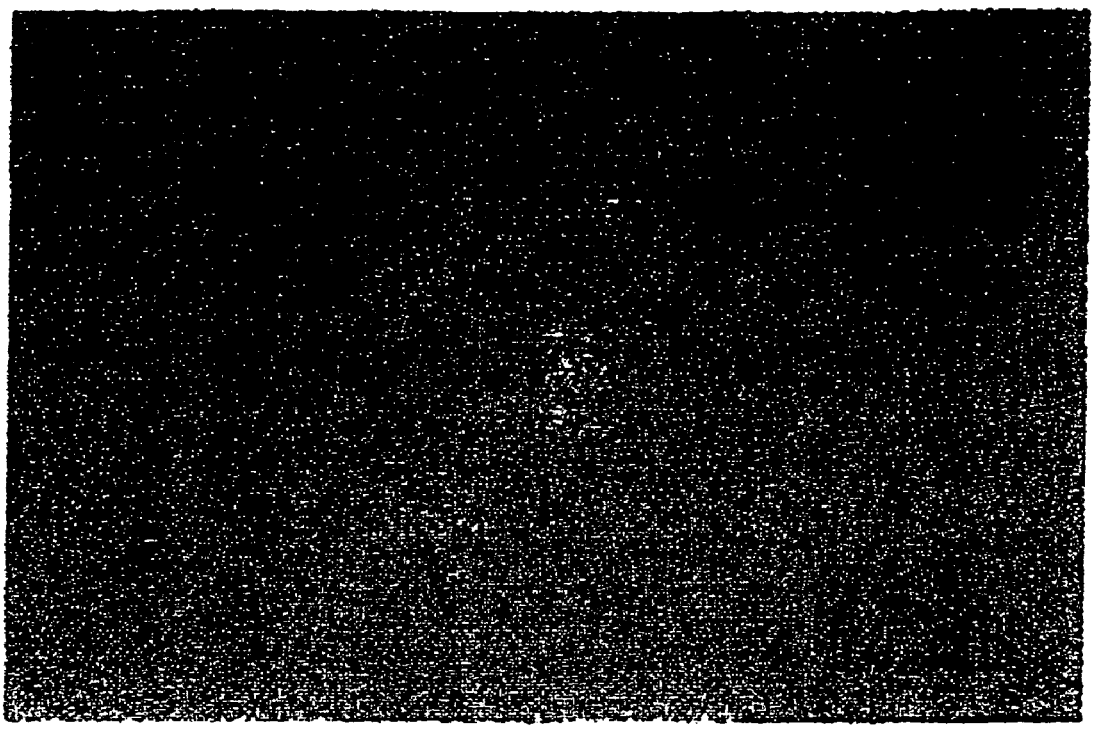
FIG. 3 shows an image of the microstructure after the solution annealing with subsequent quench.

To eliminate the disruptive precipitations, the castings are annealed in a chamber furnace under argon shielding gas atmosphere. A temperature range from approx. 780° C. to 860° C. with a duration of several hours, generally two hours, is selected for this purpose. In this context, there is a reciprocal relationship between the temperature and duration; at higher temperature, a shorter time is sufficient, and vice versa. Following the solution annealing, the castings are quenched with cold water. FIG. 3 (1000× magnification) illustrates the microstructure following the solution annealing. Primary β-grains and, within the grains, very fine inter-dendritic precipitations (cf. cloud-like accumulation in the top left of the figure) can be seen. The objects which have been investment-cast using the process according to the invention have β-grains with a mean size of more than 0.3 mm in their crystal structure. This size is typical of the crystal structure achieved by the process according to the invention.

Figure 5:
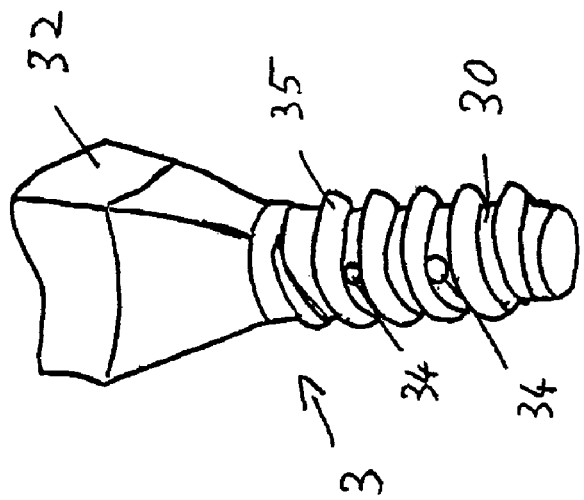
FIG. 5 shows a view of a dental implant as a further exemplary embodiment.

The mechanical properties achieved following the solution annealing are given in the table in FIG. 5.

Figure 4:
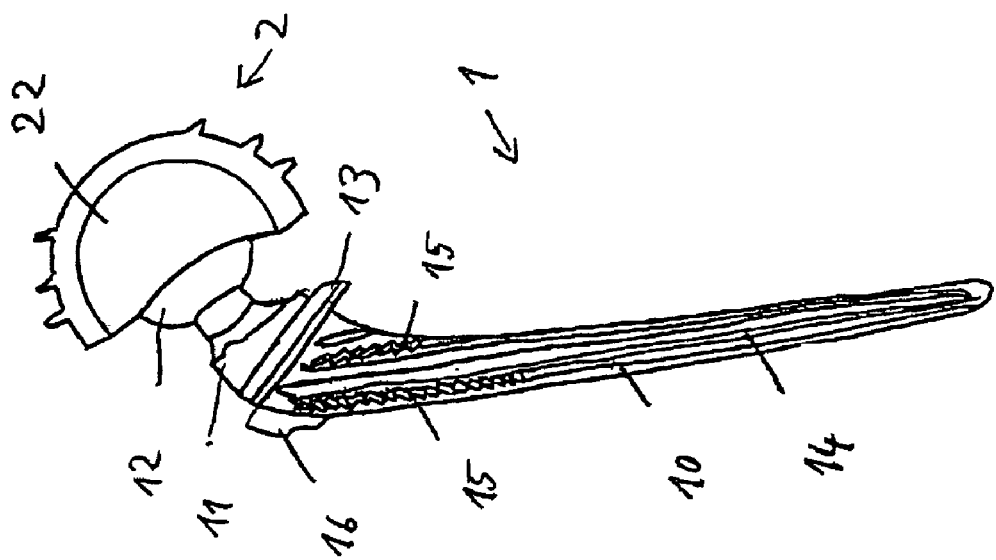
FIG. 4 shows a view of a femur part of an exemplary embodiment of an implant according to the invention.

The exemplary embodiment illustrated in FIG. 4 shows a femur part 1 of a hip prosthesis. It consists of a β-titanium alloy, namely TiMo15. It has a body-centered cubic crystal structure at room temperature.

The femur part 1 is intended for implantation at the upper end of the femur. It has an elongate shaft 10 and a neck 11 which adjoins it at an obtuse angle. At the end of the neck remote from the shaft there is a joint head 12 which, together with an acetabular part 2, forms a joint. Implantation involves complete or partial resection of the head of the fiboneck, opening up access to the medullary cavity of the femur. Via this access, the shaft 10 of the femur part 1 is introduced into the medullary cavity, where it is anchored. Depending on the particular design, cement is provided as anchoring means or the fixing takes place without the use of cement.

The femur 1 introduces mechanical loads acting on the hip prosthesis, whether the static loads when standing or dynamic loads when walking, into the femur. Physiologically compatible transmission of loads is important for permanent reliable anchoring of the femur part 1 in the bone material of the femur. If the femur part 1 is of rigid design, it absorbs a considerable portion of the load, thereby relieving the load on the bone material in particular in the upper region of the femur. In the longer term, this leads to degeneration of the femur in this region. This leads to the risk of the femur part 1 coming loose and ultimately of the prosthesis failing. To prevent this failure mode, it is favorable for the femur part 1 to be of less rigid design. In particular the shaft 10 of the femur part 1 is critical in this respect. In the cortical region, the bone material of the femur has a modulus of elasticity of approx. 20 000 to 25 000 N/mm$^2$. According to the invention, the femur part 1 has a modulus of elasticity of only approx. 60 000 N/mm$^2$. Materials which are conventionally used, such as TiAl6V4, have a modulus of elasticity of approx. 100 000 N/mm$^2$ or even 200 000 N/mm$^2$ in the case of cobalt-chromium alloys. The femur part 1 according to the invention therefore has a physiologically compatible low modulus of elasticity. The low modulus of elasticity is a major advantage for the long-term compatibility of the prosthesis in particular in the region of the shaft 10, which is critical in this respect.

The invention allows simple production of even complex shapes by investment casting. For example, the femur part 1 has a multiplicity of recesses and sawtooth-like projections on its shaft 10. These are used to improve anchoring of the femur part 1 in the femur, allowing cement-free implantation. A plurality of grooves 14 running in the longitudinal direction of the shaft 10 can be seen. They are arranged on both the anterior and posterior side of the shaft 10 but may also be provided on the lateral sides. A plurality of rows of sawtooth projections 15 are provided in the upper region of the shaft 10. Furthermore, an encircling ring 13 is provided at the transition to the neck 11. It can be designed as a separate element, but the invention means that it may also be integral with the shaft 10 and neck 11. Such complex shapes of prosthesis parts can conventionally only be produced from TiAl6V4. However, as has already been explained above, this material has an undesirably high modulus of elasticity. Although it is also known to produce femur parts from β-titanium alloys, this can only be done using the forging process. Forging cannot produce shapes which are as complex and, from a medical perspective, as advantageous as the shape illustrated in FIG. 4. The benefit of the invention is that such complex shapes can be achieved even for hip prostheses made from β-titanium alloys.

FIG. 5 illustrates a dental implant as a further exemplary embodiment. A dental implant 3 of this type has the function of an artificial foundation. It is intended to replace the natural tooth root and is used to secure dental prostheses (not illustrated) to its head 32. The dental implant 3 has to satisfy primarily two different conditions. On the one hand, it has to be able to withstand high loads. When chewing, static forces of up to 550 N can act on a tooth. These forces have to be absorbed by the dental implant as fluctuating stresses over the course of years and have to be introduced into the jaw bone. This leads to the second condition, namely that of good bonding to the bone. The introduction of the forces which occur during chewing is not without problems, especially since dental implants have only a very thin shaft 30. To achieve optimum anchoring in the jaw bone and thereby to counteract the risk of the implant coming loose, the shaft 30 is provided with a screw thread 35. The anchoring can be further improved by the provision of transverse openings 34, preferably, as through-openings. These promote growth of the dental implant into the jawbone and are therefore highly beneficial to reliable and permanent anchoring, but they do lead to stress peaks and therefore to higher mechanical loading on the shaft 30. The process according to the invention allows dental implants 3 of this type to be produced by the investment casting process from β-titanium alloys. In this context, it is possible for even complex shapes, such as the screw thread 35 and the transverse openings 34, to be produced economically without the need for complex remachining, for example by material-removing machining. Therefore, when selecting a suitable titanium alloy and during design and dimensioning, there is no need to take into account the machineability. It is in this way possible to realize designs which would be virtually impossible to realize with conventional shaping by forging or machining. Moreover, the statements which have been made above in connection with the femur prosthesis, whereby the risk of degeneration of the surrounding bone structure is minimized as a result of the low modulus of elasticity, also apply to dental implants.

The invention claimed is:
1. A process for producing a medical implant from a titanium alloy, comprising:
providing a β-titanium alloy having a molybdenum content of 12% to 16%,
investment-casting the titanium alloy in a casting mold which corresponds in configuration to the implant that is to be produced to produce an implant intermediate, hot isostatic pressing the implant intermediate at a temperature that is less than or equal to a beta-transus temperature of the β-titanium alloy and is not less than 100° C. below the beta-transus temperature, solution annealing the pressed implant intermediate at a temperature range of 700° C. to 900° C., and then quenching the solution annealed implant intermediate to produce the medical implant with a modulus of elasticity in the range of 59.4 kN/mm² and 68 kN/mm², wherein the investment-casting includes melting the alloy at a temperature of more than 1770° C.

2. The process of claim 1, which further comprises hardening following the quenching.

3. The process of claim 1, wherein the temperature profile during the solution annealing is selected in such a way that the titanium alloy is free of an w-phase.

4. The process of claim 1, wherein the quenching is carried out using cold water.

5. The process of claim 1, wherein the alloy has a molybdenum content of approximately 15%.

6. The process of claim 1, wherein the hot isostatic pressing takes place at a temperature which is at most equal to the beta-transus temperature of the alloy and is not less than 40° C. below the beta-transus temperature.

7. The process of claim 1, wherein the solution annealing is carried out at a temperature of from 780° C. to 880° C.

* * * * *

UNITED STATES PATENT AND TRADEMARK OFFICE
CERTIFICATE OF CORRECTION

PATENT NO. : 7,802,611 B2  
APPLICATION NO. : 11/370231  
DATED : September 28, 2010  
INVENTOR(S) : Sevki Baliktay et al.

It is certified that error appears in the above-identified patent and that said Letters Patent is hereby corrected as shown below:

In the Specification:

In Column 2, line 57, please replace "Ω-phases" with --ω-phases--.

In Column 2, line 59, please replace "Ω-phase" with --ω-phase--.

In Column 4, line 47, please replace "n-stabilizers" with --β-stabilizers--.

In the Claims:

In Claim 3, column 8, line 3, please replace "w-phase" with --ω-phase--.

Signed and Sealed this  
Eleventh Day of January, 2011

David J. Kappos  
*Director of the United States Patent and Trademark Office*